United States Patent [19]

Häger

[11] Patent Number: 4,597,940

[45] Date of Patent: Jul. 1, 1986

[54] PRESERVATIVE TREATMENT OF WOOD

[76] Inventor: Bror O. Häger, Forsetevagen 5, S-182 63 Djursholm, Sweden

[21] Appl. No.: 698,411

[22] Filed: Feb. 5, 1985

[30] Foreign Application Priority Data

Feb. 6, 1984 [SE] Sweden ............................... 8400584

[51] Int. Cl.[4] ................................................ A61L 9/04

[52] U.S. Cl. ........................................ 422/32; 422/40; 34/9.5; 34/13.8; 423/420; 427/254; 435/800; 162/63; 162/76; 162/90; 162/100; 162/160; 162/161

[58] Field of Search ................... 422/9, 10, 16, 28, 32, 422/40; 423/420; 427/254; 34/9.5, 13.4, 13.8; 435/800; 162/160, 161

[56] References Cited

U.S. PATENT DOCUMENTS 3,481,686 12/1969 Ivnas et al. ............................ 422/32
3,617,436 11/1971 Assarsson ................... 162/DIG. 12

OTHER PUBLICATIONS

The Condensed Chemical Dictionary, 10 Ed., Gessner G. Hawley, Van Nostrand Reinhold Comp., p. 57, 1981.
Silo-Stored Hardwood Chips Treated with Sodium Carbonate, Michael A. Hulme et al., 12/1978, pp. 47–50.

*Primary Examiner*—David L. Lacey
*Assistant Examiner*—Titus B. Ledbetter
*Attorney, Agent, or Firm*—Burns, Doane, Swecker & Mathis

[57] ABSTRACT

This invention concerns a treatment for preserving or protecting moist wood against attacks from microorganisms (fungi) with the use of evaporable or sublimable ammonium salts. The protection is obtained by distributing the salts close to the wood so that the salts form an atmosphere around the wood in which the microorganisms cannot develop. The treatment is of special interest for moist wood during a storage period until it has been dried and is not further attached by fungi.

15 Claims, No Drawings

PRESERVATIVE TREATMENT OF WOOD

BACKGROUND OF THE INVENTION

Moist wood and other cellulosic organic products which are kept in stationary air, for instance in limited spaces (rooms), in closed constructions, in piles or stacks is attacked by microorganisms, particularly fungi of various kinds. They discolor the wood and also give in other respects a less desirable appearance. Some of these fungi, especially mold, are difficult to control or eliminate. The attacks are to a high degree dependent on the temperature and the kind of fungi. Below 5° C. there are few attacks and around 45° C. and above only a few fungi can develop. Generally, the most severe fungi attacks occur at temperatures of around 25° to 30° C. Such fungi thrive in remote spaces with low air circulation and with relatively high moisture and temperatures. In such areas it is also most difficult to have contact with and treat the wood against the fungi.

The problem may simply be so defined that it is of importance to protect the wood (as long as it is moist) until it has been dried and no risk of fungi attacks is present.

In order to prevent the development of these fungi, above all the troublesome mold, many different kinds of treatments have been used. High amounts of preservative have been required to obtain satisfactory results. One method that has been successful and is of interest in connection with the present innovation has been to treat the wood with solutions of alkali metal hydroxides or sodium carbonate. Extensive experiments with alkali treatment of such products as wood chips have been published over the past 20 years. Good effects have been obtained.

During these experiments it has been observed that it is an advantage not to use alkalies of excessive strength, as these may attack the wood fibers, especially as the treated products become drier.

SUMMARY OF THE INVENTION

In accordance with the present invention, it has been found possible to control or eliminate various wood-destroying fungi by the use of ammonium salts which slowly evaporate or sublimate and form an atmosphere in which the fungi cannot develop. For obtaining good results, the salts of weak, evaporable acids are preferably used.

DETAILED DESCRIPTION OF THE INVENTION

Any suitable ammonium salt can be used, including the carbonate, acetate, propionate, benzoate, salicylate, cyanide, cyanate, nitrite, sulphite, fluoride, borofluoride and fluorosilicate. Among these the carbonate, propionate, sulphite and the three fluorides are preferred for various applications. The sulphite is preferred for the preservation of pulp and chips, and the fluorides give excellent results, but have limited use in view of environmental aspects. The cyanides, cyanates and nitrites have more limited use.

Ammonium bicarbonate is a good general purpose compound. It can be used alone or together with other salts. It does not create an environmental hazard, as its presence is observed by its smell. It acts by the presence of the ammonia, which creates a basic atmosphere unfavorable to the wood destroying fungi. Preferably, some of the carbonate is present in all mixtures in order to utilize its basic activity. The other salts which contain an active negative ion give not only an added but also a synergistic effect. They evaporate more slowly and give a persistent all around effect. A much slower evaporation is obtained with the acetate and to a still greater degree with the benzoate and the salicylate.

The invention has a broad field of applications in the protection of moist wood from destructive fungi, for example new buildings with walled-in moist wood, wood dryers—to avoid both discoloration of the wood and unhealthy working conditions—and piles of wood during storage and driving. Other applications are different storage configurations of moist wood, paper, chips and fibers of different kinds, such as pulp etc. Many different evaporable ammonium salts of weak acids can be used, either alone or in admixture.

As examples of suitable ammonium compounds useful according to the invention, the following examples can be given.

| | |
|---|---|
| 1. Ammonium bicarbonate | 100 weight percent |
| 2. Ammonium bicarbonate | 95 weight percent |
| Ammonium propionate | 5 weight percent |
| 3. Ammonium sulphite | 100 weight percent |
| 4. Ammonium bicarbonate | 50 weight percent |
| Ammonium sulphite | 50 weight percent |
| 5. Ammonium bicarbonate | 50 weight percent |
| Ammonium bifluoride | 50 weight percent |

The treatment is simple. The preserving mixture is distributed appropriately in the walled-in spaces with wood, in drying chambers, in wood piles, chip storage areas, etc., on or close to the wood material. The mixture can be introduced in dry form, or applied as a water solution, as by brushing or spraying. The mixture evaporates or sublimes to give a protective atmosphere. The required dosage is surprisingly low, since only a small amount of preserving mixture provides the desired vapor pressure. A larger amount of preserving mixture provides this pressure sooner, but this is of less importance, since it involves only a transition period. Preferably, an appropriate amount of solid mixture remains in the space at all times producing vapors. For a long term effect a larger amount, or repeated small amounts, of mixture should be introduced.

To a certain degree conditions in spaces where the preserving mixture is used are automatically regulated by the properties of the salts used. If the space where the wood is has poor ventilation or high temperature or both, with high risks for strong fungi attacks, at the same time the possibilities for obtaining a high vapor mixture pressure will be increased, producing an improved protective effect, while the opposite will happen when some air ventilation exists and/or when the temperature is lower.

As a common rule it may be said that for space volumes of up to one cubic meter one kilogram or less of the preservative mixture is sufficient for normal use. If the space is closed, and contains less material to be protected, the furnished mixture will last for a long time. On the other hand, if ventilation exists in a space with stored moist material which absorbs vapor the mixture will gradually be consumed. This has to be considered in the dosage; enough of the mixture has to be added at the start to protect the wood until it dries, or the dosage repeated periodically.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

I claim:

1. A method for protecting cellulosic products selected from the group consisting of moist wood, paper, pulp, chips, fibers, and other organic cellulosic products against damage from microorganisms including fungi, said method comprising a step of introducing an evaporable ammonium salt of a weak acid into a limited space in which said products are stored and allowing it to evaporate to provide a protective atmosphere against the microorganisms.

2. A method according to claim 1 wherein said ammonium salt comprises at least one ammonium salt selected from the group consisting of bicarbonate, acetate, propionate, benzoate, nitrite, sulphite, fluoride, borofluoride and fluorosilicate.

3. A method according to claim 1 wherein said ammonium salt comprises at least one ammonium salt selected from the group consisting of bicarbonate, propionate, sulphite, fluoride, borofluoride and fluorosilicate.

4. A method according to claim 1 wherein said ammonium salt consists essentially of ammonium bicarbonate.

5. A method according to claim 1, wherein said ammonium salt is a mixture of ammonium carbonate and at least one ammonium salt selected from the group consisting of ammonium acetate, propionate, benzoate and sulphite.

6. A method according to claim 1 wherein said protective atmosphere is a basic atmosphere comprising ammonia formed by the evaporation of said ammonium salt.

7. A method according to claim 1 wherein said ammonium salt comprises at least one ammonium salt selected from the group consisting of carbonate, salicylate, cyanide and cyanate.

8. A method according to claim 1 wherein said ammonium salt comprises a mixture of ammonium bicarbonate with at least one ammonium salt selected from the group consisting of ammonium acetate, propionate, benzoate, nitrite, sulphite, fluoride, borofluoride, bifluoride and fluorosilicate.

9. A method according to claim 1 wherein the step of introducing comprises treating said product with a water solution of said ammonium salt.

10. A method according to claim 9 wherein the step of introducing comprises applying said water solution of said ammonium salt by spraying or brushing.

11. A method according to claim 9 wherein said ammonium salt comprises at least one ammonium salt selected from the group consisting of bicarbonate, acetate, propionate, benzoate, nitrite, sulphite, fluoride, borofluoride and fluorosilicate.

12. A method for protecting cellulosic products selected from the group consisting of moist wood, paper, chips, fibers, and other organic cellulosic products stored in a pile against damage from microorganisms including fungi, said method comprising a step of introducing an evaporable ammonium salt of a weak acid into said pile and allowing it to evaporate to form ammonia and to provide a protective atmosphere comprising ammonia against the microorganisms.

13. A method according to claim 12 wherein said ammonium salt comprises at least one ammonium salt selected from the group consisting of bicarbonate, carbonate, acetate, propionate, benzoate, nitrite, sulphite, fluoride, bifluoride, borofluoride and fluorosilicate.

14. A method according to claim 12 wherein said step of introducing said ammonium salt comprises treating said products with a water solution of said ammonium salt.

15. A method of protecting cellulosic products selected from the group consisting of moist wood, paper, chips, pulp, fibers and other organic cellulosic products against damage from microorganisms including fungi, said method comprising a step of distributing closely adjacent to said products an evaporable ammonium salt, comprising at least one ammonium salt selected from the group consisting of bicarbonate, carbonate, acetate, propionate, benzoate, nitrite, sulphite, fluoride, borofluoride and fluorosilicate, allowing said salt to evaporate to from ammonia and to provide a protective atmosphere comprising ammonia against the microorganisms, and maintaining said atmosphere about said products to prevent said damage.

* * * * *